United States Patent [19]

Bedi et al.

[11] Patent Number: 4,531,522

[45] Date of Patent: Jul. 30, 1985

[54] TWO-PIECE TISSUE FASTENER WITH LOCKING TOP AND METHOD FOR APPLYING SAME

[75] Inventors: James J. Bedi, Stockton, N.J.; Madhusudan Joshi, E. Aurora, N.Y.

[73] Assignee: Ethicon, Inc., Somerville, N.J.

[21] Appl. No.: 506,143

[22] Filed: Jun. 20, 1983

[51] Int. Cl.³ .............................................. A61B 17/08
[52] U.S. Cl. ................................ 128/335; 128/334 C; 128/337; 227/DIG. 1
[58] Field of Search ............ 128/346, 337, 335, 334 R, 128/334 C, 330, 325, 326; 227/DIG. 1, 15–18, 77; 3/1; 411/469, 457, 451, 456, 455, 362–364, 360, 501, 506; 24/150 FP, 297, 16 PB, 580, 581, 584, 697, 30.5 P, 453, 537, 515, 513, 503, 94–96; 40/300, 301

[56] References Cited

U.S. PATENT DOCUMENTS

| 3,570,497 | 3/1971 | Lemole | 128/339 X |
| 4,317,451 | 3/1982 | Cerwin et al. | 128/337 X |
| 4,458,682 | 7/1984 | Cerwin | 128/346 X |

FOREIGN PATENT DOCUMENTS 456458 11/1936 United Kingdom ............... 128/337

Primary Examiner—Michael H. Thaler
Attorney, Agent, or Firm—Robert L. Minier

[57] ABSTRACT

A fastener is provided to hold together portions of mammalian tissue and includes a fastening member and a retainer adapted to receive legs of the fastening member that are inserted through the tissue portions. The legs of the fasteneing member are hinged and are pivoted toward one another when the retainer is applied so as to draw and hold the tissue portions together.

13 Claims, 10 Drawing Figures

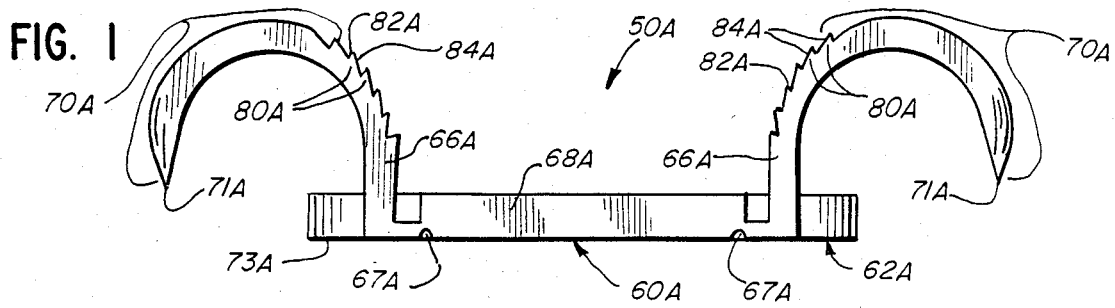
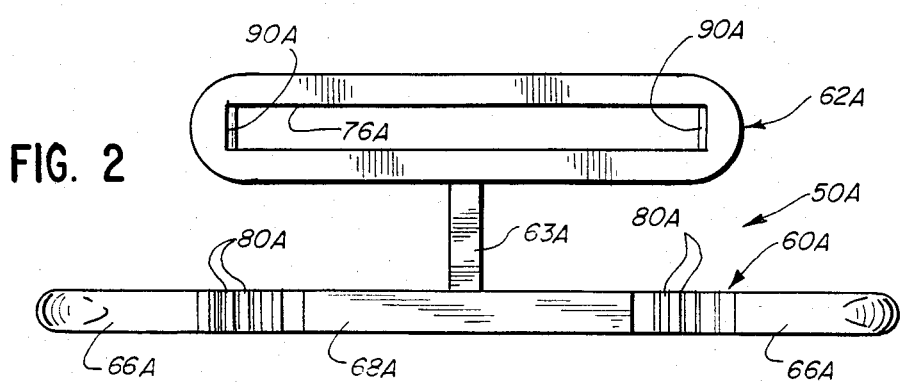
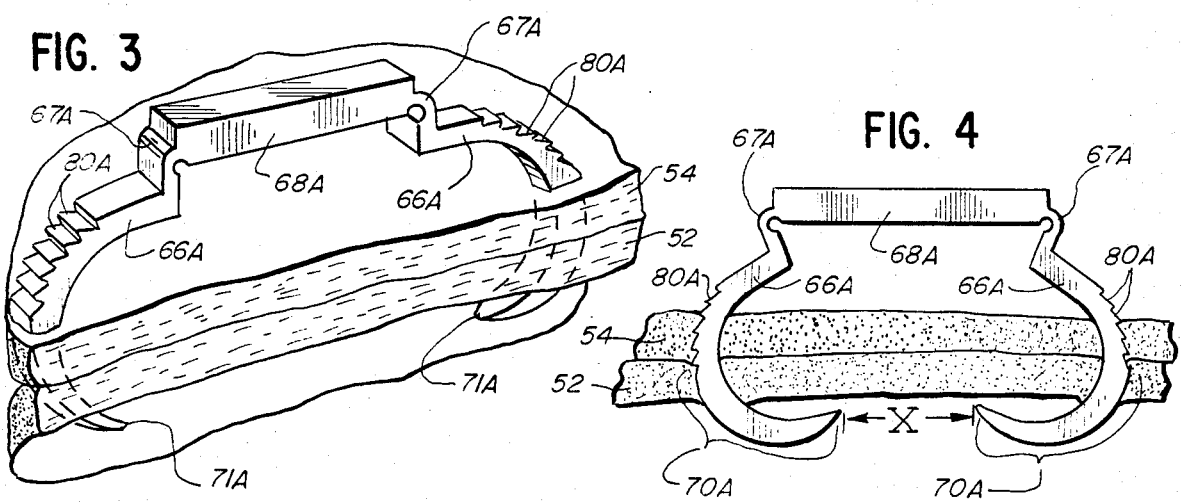
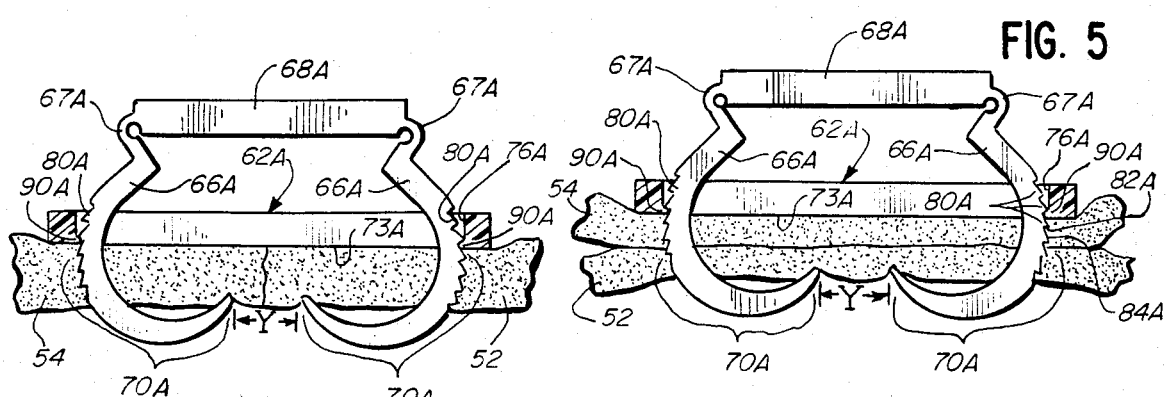

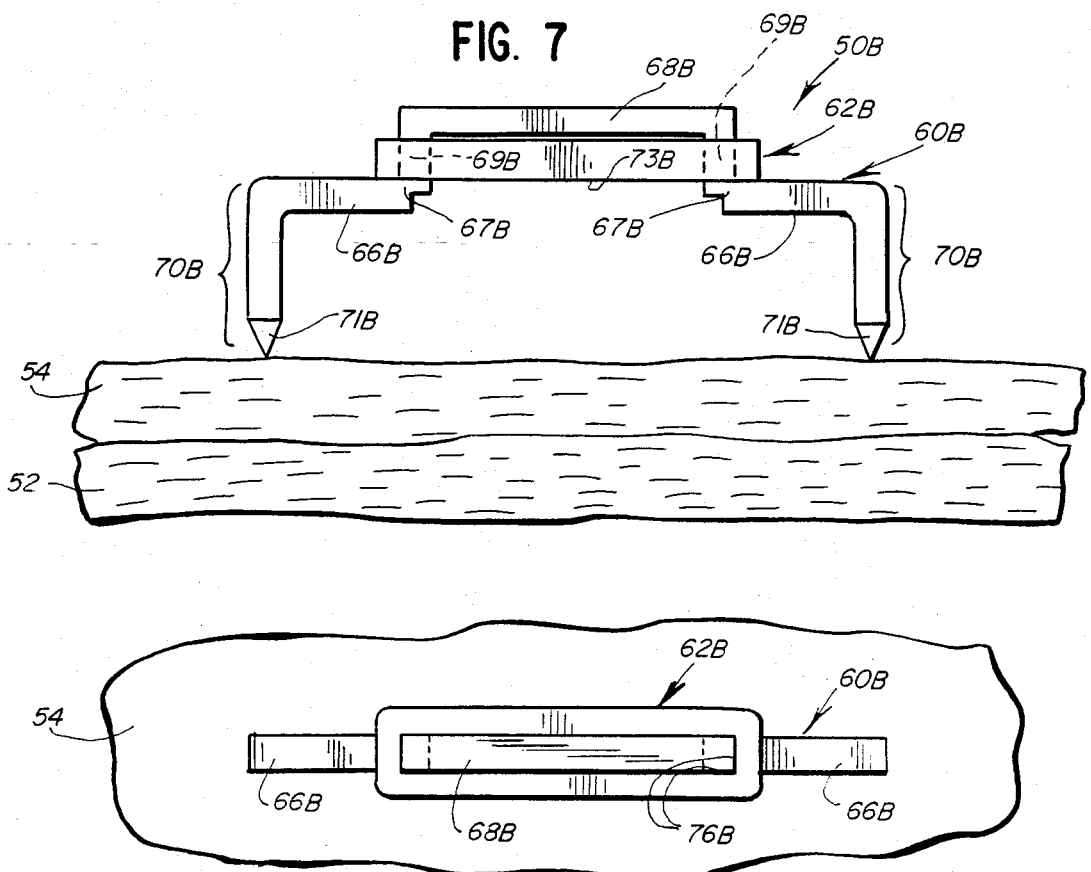
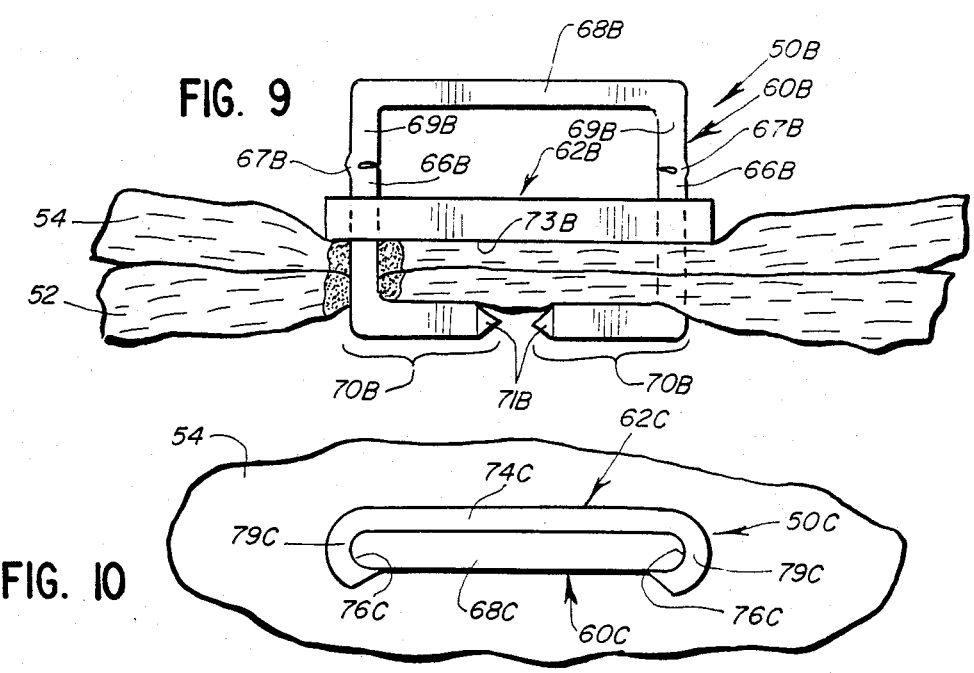

TWO-PIECE TISSUE FASTENER WITH LOCKING TOP AND METHOD FOR APPLYING SAME

TECHNICAL FIELD

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International Patent Application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The fastener strip prongs each include a plurality of spaced-apart engaging members for engaging the retainer strip at a desired position relative to the prongs. This provides for the capability of adjusting the distance between the fastener strip and the retainer strip. Such a fastening device may be fabricated from a biodegradable or absorbable material.

Yet another tissue fastening device having a plurality of components is disclosed in co-pending commonly assigned U.S. patent application U.S.S.N. 349,433, filed Mar. 18, 1982. The fasteners disclosed in that application are made from various polymeric materials and the legs of the U-shaped staple portion of the fastener have a taper to improve the penetration of the staple into tissue.

Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. It would be especially desirable to provide such a fastener that could be effective to hold tissue portions together in either (1) an edge butting relationship or (2) an overlapping (lapped) relationship.

Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

Further, it would be beneficial if such an improved fastener had a configuration that would enable the fastener to be fabricated with (1) as small a size as possible to minimize dosage and (2) with a minimum of sharp edges or protrusions. Also, another desirable feature of such an improved fastener would be a fastener configuration that did not form, or contribute to the formation of, pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide such a fastener with a design that would facilitate its application to the tissue portions with a simple yet effective method.

SUMMARY OF THE INVENTION

An improved fastener is provided to hold together portions of mammalian tissue, such as are defined by a wound or incision, to facilitate healing of the wound or incision. The fastener comprises a fastening member and a retainer.

The fastening member includes a link member and a pair of spaced-apart legs hingedly connected to the link member. The link member is adapted to be disposed on one side of at least one of the tissue portions. Each leg of the fastening member has a distal end portion adapted to be engaged with an oppositely facing side of one of the tissue portions opposite the link member. Each leg distal end portion terminates in a configuration adapted to penetrate the tissue portions.

The retainer is adapted to receive the fastening member legs. The retainer defines an engaging surface for engaging at least one of the tissue portions and defines means for engaging the fastening member legs.

A novel process is used to apply the fastener to the tissue portions. The tissue portions are first approximated. The tissue portions are next penetrated with the fastening member legs.

Then the retainer is disposed on one side of at least one of the tissue portions to engage the fastening member legs with the retainer leg engaging means. This pivots the fastening member legs toward one another in engagement with the tissue portions. In this manner, the fastening member legs hold the tissue portions together while the retainer inhibits withdrawal of the fastening member.

Numerous other features of various embodiments of a novel tissue fastener and application methods will be apparent from the following detailed description and accompanying drawings.

BRIEF DESCRIPTION OF THE DRAWINGS

In the accompanying drawings forming part of the specification, and in which like numerals are employed to desginate like parts throughout the same, FIG. 1 is a side view of a first embodiment of the fastener of the present invention;

FIG. 2 is a top plan view of the first embodiment of the fastener shown in FIG. 1;

FIG. 3 is a fragmentary, perspective view of two portions of mammalian tissue defined by an incision or wound in overlapping or lapped relationship and being penetrated by the fastening member of the first embodiment of the fastener shown in FIGS. 1 and 2;

FIG. 4 is a view similar to FIG. 3, but taken from the side with the tissue portions shown in cross section to better illustrate the orientation of the fastening member of the fastener as it is initially disposed in the tissue portions;

FIG. 5 is a view similar to FIG. 4, but showing the retainer assembled with the fastening member;

FIG. 6 is a side view of the assembled fastening member and retainer of FIGS. 1-5 shown holding together two tissue portions in an edge butting relationship;

FIG. 7 is a side view of a second embodiment of the fastener shown in a position disposed adjacent two lapped tissue portions prior to being applied to the tissue portions;

FIG. 8 is a top plan view of the second embodiment of the fastener of FIG. 7;

FIG. 9 is a side view of the second embodiment of the fastener shown fully applied to, and engaged with, the tissue portions to hold the tissue portions together; and FIG. 10 is a top plan view of a third embodiment of the fastener applied to the tissue portions.

DESCRIPTION OF THE PREFERRED EMBODIMENTS

This invention may be used in many different forms. The specification and accompanying drawings disclose only a few specific forms as an example of the use of the invention. The precise shapes and sizes of the components herein described are not essential to the invention unless otherwise indicated. The invention is not intended to be limited to the embodiments illustrated, and the scope of the invention will be pointed out in the appended claims.

FIRST EMBODIMENT OF THE FASTENER

A first embodiment of the fastener is illustrated in FIGS. 1 and 2 and is designated generally therein by reference numeral 50A. The fastener is shown in FIGS. 3 and 4 being applied to overlapping or lapped mammalian tissue portions 52 and 54, such as are defined by a wound or incision.

The fastener 50A is illustrated in FIGS. 5 and 6 in the fully assembled, "set" configuration. The fastener 50A is shown holding together the two tissue portions 52 and 54—in lapping relationship in FIG. 5 and in edge butting relationship in FIG. 6—to facilitate healing of the wound or incision. Typically, a plurality of such fasteners 50A would be used to close a wound or incision. However, with just a small wound or incision, one fastener 50A may be sufficient.

The fastener 50A includes two components, a fastening member 60A and a retainer 62A, which may be initially provided in an unassembled state as illustrated in FIGS. 1 and 2 and which are adapted to be subsequently assembled to cooperate in holding the tissue portions together.

In one form of the invention, the retainer 62A may be initially secured or connected to the fastening member 60A by means of a connecting member 63A as illustrated in FIG. 2. When it is desired to apply the fastener 50A to the tissue portions, the retainer 62A is first separated from the fastening member 60A by severing or breaking the connecting member 63A.

Alternatively, the retainer 62A and the fastening member 60A may be initially provided to the user as completely separate and unattached components. However, providing the fastener 50A in the form of a fastening member 60A and retainer 62A joined by the connecting member 63A has the obvious advantage of conveniently maintaining both components together during storage and handling prior to use.

As best illustrated in FIGS. 1 and 2, the fastening member 60A comprises a link member 68A and a pair of spaced-apart legs 66A which are hingedly connected to the link member 68A. As illustrated in FIG. 3, the link member 68A is adapted to be disoosed on one side of at least one of the tissue portions (e.g., tissue portion 54 in FIG. 3).

Each leg 66A has a distal end portion 70A adapted to be engaged with an oppositely facing side of one or more tissue portions (e.g., tissue portion 52 in FIG. 5 or both tissue portions 52 and 54 in FIG. 6). Each leg distal end portion 70A terminates in a point or end configuration 71A adapted to penetrate the tissue portions Preferably, the fastening member is molded from a thermolplastic polymer with a living hinge 67A hingedly connecting each fastening member leg 66A with the fastening member link member 68A.

In the first embodiment illustrated in FIG. 1, each leg 66A of the fastening member 60A is preferably arcuate and has a row of teeth 80A. The teeth 80A on one leg 66A of the fastening member 60A are oppositely facing from the teeth on the other leg of the fastening member when the fastening member is properly applied to the tissue portions in the final orientation illustrated in FIGS. 5 or 6 in a manner that will be described in detail hereinafter. Preferably, each tooth 80A has, or is defined by, a short latching surface 82A and a longer camming surface 84A (FIG. 1).

The retainer 62A has a slot 76A for receiving the fastening member legs 66A. The retainer 62A defines an engaging surface 73A for engaging at least one of the tissue portions (e.g., the overlapping tissue portion 54 in FIG. 5 or both edge butting tissue portions 54 and 52 in FIG. 6).

The retainer 62A also defines means for engaging the fastening member legs 66A, and, in the embodiment illustrated in FIGS. 1-6, such leg engaging means is defined at the periphery of the slot 76A in the retainer 62A by a lip 90A at each end of the slot 76A. Each lip 90A extends inwardly into the slot 76A.

The fastening member 60A and retainer 62A may be formed from suitable materials, such as thermolplastic polymer materials that are absorbable by mammalian tissue. For example, the fastening member and retainer could be molded from absorbable polymers or copolymers of poly-dioxanone, lactide, glycolide, and the like. The fastener 50A may also be molded from a combination of such materials The fastener 50A is used to join the tissue portions 52 and 54 in a novel manner. First, if the retainer 62A is joined to the fastening member 60A by a connecting member 63A, the connecting member 63A is broken to separate the two components. Then, the tissue portions 52 and 54 are first approximated in either a surface-to-surface lapped relationship as illustrated in FIGS. 3–5 or in an edge butting relationship as illustrated in FIG. 6.

Next, the fastening member 60A is applied to the tissue portions by penetrating the tissue portions with the fastening member legs 66A. This may be effected as illustrated in FIG. 3 with the tissue portions 54 and 52 in a lapped relationship. The point 71A of each leg 66A is pushed through the tissue portions from one side and, after the point 71A emerges from the other side, it may be gripped with a forceps if desired and pulled to achieve the desired penetration of the tissue portions. On the other hand, each leg 66A may be pushed entirely from one side of the tissue portions to achieve the desired penetration.

According to the method for applying the fastener 50A, the tissue portions are penetrated with the legs 66A so that the legs are initially spaced apart (e.g., by a first distance X as illustrated in FIG. 4). To aid in effecting this penetration, the fastening member legs 66A may be initially pivoted apart by a distance greater than the first distance X so that the leg ends or points 71A can be more easily inserted into the tissue portions To this end, the legs 66A may be initially pivoted or spaced apart to the orientation illustrated in FIG. 1. In this orientation, the fastening member 60A can be easily placed adjacent the tissue portions so that the pointed ends 71A of the legs 66A can be pressed into the tissue portions as illustrated in FIGS. 3 and 4.

When the legs 66A have been inserted the desired amount into the tissue portions so that they are spaced apart by the first distance X in the orientation generally illustrated in FIG. 4, the retainer 62A is then disposed on the fastening member 60A. The retainer 62A is inserted over the link member 68A and around the fastening member legs 66A (FIGS. 5 and 6). Then the retainer 62A is moved along the legs 66A toward the distal ends of the legs while engaged with the legs.

Specifically, the lips 90A at each end of the retainer 62A engage the exterior of a leg 66A. Each lip 90A slides along the leg and along the camming surfaces 84A of the leg teeth 80A. As the retainer 62A is pushed further and further along the legs 66A, the legs 66A are pivoted inwardly toward one another so that the legs 66A are spaced apart by a second distance Y (FIGS. 5 and 6) that is less than the first distance X Further, as the legs 66A are pivoted inwardly, the distal end portions 70A of each leg engage one of the tissue portions as best illustrated in FIGS. 5 and 6. This tends to force the tissue portions together. The retainer 62A is preferably moved along the fastening member legs 66A by an amount sufficient to cause some compression of the tissue portions between the engaging surface 73A of the retainer 62A and the distal end portions 70A of the fastening member legs 66A.

When the retainer 62A has been moved along the fastening member legs 66A to the desired position, the retainer lips 90A engage the locking surface 82A of an adjacent tooth 80A. In this manner, the retainer 62A is latched against the fastening member legs 66A to cause the tissue portions to be held together and to inhibit withdrawal of the fastening member 60A.

SECOND EMBODIMENT OF THE FASTENER

The second embodiment of the fastener is illustrated in FIGS. 7–9 and is designated generally therein by reference numeral 50B. The fastener 50B includes a fastening member 60B and a retainer 62B.

The fastener 50B is similar to, and functions in a somewhat similar (though not identical) manner, to the first embodiment of the fastener 50A described above with reference to FIGS. 1–6. The elements of the second embodiment of the fastener 50B that are functionally analogous to those of the first embodiment of the fastener 50A are designated by reference numerals identical to those used for the first embodiment with the exception that the second embodiment reference numerals are followed by the upper case letter B whereas the first embodiment reference numerals are followed by the upper case letter A.

The fastener 50B includes a fastening member 60B which comprises a link member 68B and a pair of spaced-apart legs 66B. Each leg 66B has a distal end portion 70B which is adapted to be engaged with a side of at least one of the tissue portions opposite the link member 68B as best illustrated in FIG. 9. The legs 66B are hingedly connected to the link member 68B by a hinge 67B. Preferably, the fastening member 60B is molded from a thermoplastic polvmer with each hinge 67B being a living hinge.

The fastening member link member 68B has a generally rectangular or square cross-section. Similarly, each of the fastening member legs 66B has a generally rectangular or square cross-section except for an end configuration or point 71B of each leg which is adapted to penetrate the tissue portions.

Unlike the first embodiment of the fastener 50A described above, the second embodiment of the fastener 50B has legs 66B which do not have teeth along a portion of their exterior In this second embodiment, reliance is placed upon frictional engagement forces to maintain the fastener 50B clamping the tissue portions as described in detail hereinafter Further, the fastening member legs 66B need not be arcuate but may be formed with an angular configuration, such as the generally right angle configuration illustrated in FIGS. 7 and 9.

A retainer 62B is provided to cooperate with the fastening member 60B when the fastening member 60B is applied to the tissue portions. Initially, the retainer 62B may be supplied to the user partially installed on the fastening member 60B as illustrated in FIG. 7. The retainer 62B includes a generally elongate slot 76B (FIG. 8) and the slot 76B may be disposed over the link member 68B and around extensions 69B of the link member 68B.

The configuration and dimensions of the slot 76B may be such that, in relation to the configuration and dimensions of the fastening member 60B, there is sufficient frictional engagement between the retainer 62B and the fastening member 60B in the orientation shown in FIG. 7 so that the retainer 62B does not easily fall off of, or become disengaged from, the fastening member 60B.

The fastener 50B is applied to the tissue portions in a manner somewhat similar to the method for applying the first embodiment of the fastener 50A described above with reference to FIGS. 3–6. Specifically, with reference to FIG. 7, the second embodiment of the fastener 50B is shown being applied to two tissue portions 54 and 52 which are in a lapped relationship and which have been approximated in surface-to-surface relationship. Alternatively, the tissue portions could be oriented and approximated in an edge abutting relationship as illustrated in FIG. 6.

In any case, after the tissue portions 54 and 52 are approximated, the fastening member 60B is applied to the tissue portions by penetrating the tissue portions with the fastening member legs 66B. To facilitate this operation, the legs 66B may be initially pivoted outwardly from each other to the general orientation illustrated in FIG. 7. Then the legs 66B are pushed into the tissue portions so that the legs are spaced apart by a first distance with the link member 68B being located on one side of the tissue portions and with the leg distal end portions 70B being located on the other side of the tissue portions.

Next, the retainer 62B, which may have previously been disposed on the top portion of the fastening member 60B as illustrated in FIG. 7, is urged downwardly along the fastening member legs 66B to cause the legs to pivot toward each other. This pivoting action is in addition to any pivoting movement that may have occurred during the initial insertion of the legs 66B through the tissue portions which may have been effected so as to initially pivot the legs 66B toward each other to the first spaced-apart distance In any case, movement of the retainer 62B along the legs 66B causes the legs to pivot toward one another further so that they are spaced apart by a second distance which is less than the first distance and so that the leg distal end portions 70B engage at least one of the tissue portions as illustrated in FIG. 9. The tissue portions 54 and 52 are thus forced together and/or compressed as desired, depending upon how far along the fastening member legs the retainer 62B is moved Owing to the tendency of the tissue portions to expand outwardly some amount, the fastening member legs 66B are urged against the ends of the retainer slot 76B and into frictional engagement with the retainer 62B. The frictional engagement is sufficient to overcome the tendency of the tissue portions to cause a reverse relative movement between the retainer 62B and the fastening member 60B. The retainer 62B thus inhibits withdrawal of the fastening member 60B.

THIRD EMBODIMENT OF THE FASTENER

FIG. 10 is a top view of the third embodiment of the fastener designated generally by the reference numeral 50C. The fastener 50C is similar to the second embodiment of the fastener 50B described above with reference to FIGS. 7–9, and includes a fastening member 60C and a retainer 62C.

The fastening member 60C is similar to the fastening member 62B described above with reference to FIGS. 7–9 except that the fastening member 60C has a link member 68C with a generally circular cross-section and has legs (not visible in FIG. 10) which also have a generally circular cross-section.

The retainer 62C includes a central bar 74C with a pair of arcuate arms 79C. Each arcuate arm 79C defines a receiving region 76C for receiving one of the fastening member legs and constitutes a means for engaging the fastening member leg. The configuration and size of each of the receiving regions 76C is selected, relative to the configuration and size of the fastening member link member 68C and legs, so as to provide a frictional engagement between the retainer 62C and the fastening member 60C.

The fastener 50C is applied to the tissue portions in a manner basically similar and analagous to that described above with reference to FIGS. 7-9 for the second embodiment of the fastener 50B. Specifically, the fastening member legs are spread apart and then inserted into the tissue portions As the tissue portions are penetrated by the fastening member legs, the legs are pivoted toward one another until they are spaced apart by a first distance.

The retainer 62B, if not initially provided on the top of the fastening member 60C, is disposed on the fastening member 60C to receive the fastening member legs. The fastening member legs are engaged with the leg engaging means or receiving regions 76C of the retainer 62B to further pivot the fastening member legs toward one another until they are spaced apart by a second distance that is less than the first distance. In this orientation, at least part of each leg distal end portions engages one of the tissue portions so that the legs hold the tissue portions together while the retainer inhibits withdrawal of the fastening member

OTHER DESIRABLE FEATURES OF THE FASTENER

Both the second and third embodiments of the fastener 50B and 50C, respectively, may be fabricated from the same materials described above for use in fabricating the first embodiment of the fastener 50A.

With each of the fastener embodiments and modifications thereof described above, it is seen that the fastener can accommodate various thicknesses of tissue. Relative movement may be effected between the fastening member and retainer until the desired tissue approximation or compression is achieved. The components lock together at any of a plurality of closely spaced points along the length of the fastening member legs so that a wide range of adjustability is conveniently provided.

From the foregoing, it will be observed that numerous variations and modifications may be effected without departing from the true spirt and scope of the novel concept of the invention. It is to be understood that no limitation with respect to the specific articles, instruments, and methods described herein is intended or should be inferred. It is, of course, intended to cover by the appended claims all such modifications as fall within the scope of the claims.

What is claimed is:

1. A fastener adapted to hold together two portions of mammalian tissue, such as are defined by a wound or incision, to facilitate healing of the wound or incision, said fastener comprising:

a fastening member comprising a link member and a pair of spaced-apart legs hingedly connected to said link member, each said leg members being generally arcuate, said link member being adapted to be disposed on one side of at least one of said tissue portions, each said leg having a distal end portion adapted to be engaged with an oppositely facing side of one of said tissue portions opposite said link member, each said leg distal end portion terminating in a configuration adapted to penetrate said tissue portions; and a retainer adapted to receive said fastening member legs, said retainer defining an engaging surface for engaging at least one of said tissue portions and defining means for engaging said fastening member legs whereby said fastening member may be applied to said tissue portions by penetrating said tissue portions with said legs so that said legs are spaced apart in said tissue portions by a first distance and whereby said retainer may thereafter be engaged with said fastening member legs to pivot said fastening member legs toward one another so that they are spaced apart by a second distance less than said first distance with at least part of each said leg distal end portion engaging one of said tissue portions and with said legs holding said tissue portions together while said retainer inhibits withdrawal of said fastening member.

2. The fastener in accordance with claim 1 in which each said leg has a row of teeth and in which the teeth on one leg of the fastening member are oppositely facing from the teeth on the other leg of the fastening member when the fastening member is properly applied to the tissue portions.

3. The fastener in accordance with claim 2 in which each said tooth is defined by a camming surface and a latching surface and in which said retainer means for engaging said fastening member legs includes two lips each adapted to slide along the camming surfaces of the fastening member teeth and to engage the latching surface of one of the teeth.

4. The fastener in accordance with claim 1 in which said fastening member is molded from an absorbable thermoplastic polymer with a living hinge hingedly connecting each of said fastening member legs with said fastening member link member.

5. The fastener in accordance with claim 1 in which said retainer is initially joined to said fastening member by a connecting member which may be subsequently severed to permit the application of said retainer and said fastening member in combination to said tissue portions.

6. The fastener in accordance with claim 1 in which said retainer is molded from an absorbable thermoplastic polymer.

7. The fastener in accordance with claim 1 in which said leg engaging means of said retainer is defined at the periphery of a slot in said retainer and includes a lip at each end of said slot extending inwardly into said slot.

8. A method for holding together two portions of mammalian tissue such as are defined by a wound or incision, to facilitate the healing of the wound or incision, said method comprising the steps of:
(a) approximating said tissue portions;
(b) providing a fastening member comprising a link member and a pair of spaced-apart legs hingedly connected to said link member, said legs being generally arcuate, each said leg having a distal end portion adapted to be engaged with a side of one of said tissue portions and terminating in a configuration adapted to penetrate said tissue portions;
(c) applying said fastening member to said tissue portions by penetrating said tissue portions with said legs so that said legs are spaced apart in said tissue portions by a first distance and so that said link member is disposed on one side of at least one of said tissue portions;
(d) providing a retainer to receive said fastening member legs, said retainer defining an engaging surface for engaging at least one of said tissue portions and defining means for engaging said fastening member legs; and
(e) disposing said retainer on said fastening member to receive said fastening member legs and engaging said fastening member legs with said fastening member legs toward one another so that they are spaced apart by a second distance less than said first distance with at least part of each said leg distal end portion engaging one of said tissue portions and with said legs holding said tissue portions together while said retainer inhibits withdrawal of said fastening member.

9. The method in accordance with claim 8 in which step (a) includes arranging said tissue portions in an edge butting relationship.

10. The method in accordance with claim 8 in which step (a) includes arranging said tissue portions in a lapped relationship.

11. The method in accordance with claim 8 in which said retainer defines a slot, in which said leg engaging means of said retainer is defined at the periphery of said slot in said retainer and includes a lip at each end of said slot extending inwardly into said slot, and in which step (e) includes inserting said retainer over said fastening member legs and then moving said retainer along said legs toward the distal ends of said legs.

12. The method in accordance with claim 8 in which step (c) includes initially pivoting said fastening member legs apart by a distance greater than said first distance to facilitate tissue penetration and then penetrating said tissue portions to bring said legs into an orientation wherein the legs are spaced apart by said first distance.

13. The method in accordance with claim 8 in which step (d) includes moving said retainer relative to said fastening member legs while engaged with said legs to pivot said legs toward one another an amount sufficient to effect compression of said tissue portions.

* * * * *